(12) United States Patent
Tice et al.

(10) Patent No.: US 7,473,431 B2
(45) Date of Patent: *Jan. 6, 2009

(54) INJECTABLE METHADONE, METHADONE AND NALTREXONE, OR BUPRENORPHINE AND NALTREXONE MICROPARTICLE COMPOSITIONS AND THEIR USE IN REDUCING CONSUMPTION OF ABUSED SUBSTANCES

(75) Inventors: Thomas R. Tice, Birmingham, AL (US); Jay K. Staas, Alabaster, AL (US); Teresa M. Ferrell, Vestavia Hills, AL (US); Peter Markland, Birmingham, AL (US)

(73) Assignee: Brookwood Pharmaceuticals, Inc., Birmingham, AL (US)

( * ) Notice: Subject to any disclaimer, the term of this patent is extended or adjusted under 35 U.S.C. 154(b) by 598 days.

This patent is subject to a terminal disclaimer.

(21) Appl. No.: 10/324,062

(22) Filed: Dec. 17, 2002

(65) Prior Publication Data
US 2003/0152638 A1 Aug. 14, 2003

Related U.S. Application Data

(63) Continuation of application No. 09/648,255, filed on Aug. 25, 2000, now Pat. No. 6,495,155.

(60) Provisional application No. 60/151,112, filed on Aug. 27, 1999.

(51) Int. Cl.
*A61F 2/00* (2006.01)
(52) U.S. Cl. .................. 424/426; 424/425; 424/424; 424/497
(58) Field of Classification Search ........... 424/426, 424/489, 423, 424, 425, 497; 264/4.3, 4.6; 427/213.32, 213.36; 514/811, 812
See application file for complete search history.

(56) References Cited

U.S. PATENT DOCUMENTS

| | | | |
|---|---|---|---|
| 4,464,378 A | 8/1984 | Hussain et al. | |
| 4,652,441 A * | 3/1987 | Okada et al. | 424/497 |
| 5,143,661 A * | 9/1992 | Lawter et al. | 264/4.3 |
| 5,486,362 A | 1/1996 | Kitchell et al. | |
| 5,716,631 A | 2/1998 | Drizen et al. | |
| 5,858,388 A | 1/1999 | Grossman et al. | |
| 5,919,473 A * | 7/1999 | Elkhoury | 424/422 |
| 6,495,155 B1 * | 12/2002 | Tice et al. | 424/426 |

OTHER PUBLICATIONS

Strain et al., *J. Clinical Psychopharmcol.*, 1996, 16.58-67.
O'Connor et al., *Ann. Intern. Med.*. 1997, 127:526-30.
Kranzler et al., *Alcoholism:Clinical & Experimental Research*, 1998, 22:1074-1079.
Reuning et al., NIDA Re: Monograph Series, Jan. 1976, (4) p. 43-5.
Reuning et al., *J Pharmacokinetics & Biopharmaceutics*, Aug. 1983, 11 (4). p. 369-87.
MacGregor et al., *J. Pharm. Pharmacol.*, Jan. 1983, 35(1) p. 38-42.
Reuning et al., NIDA Res Monograph Series 1980, 28, p. 172-84.
Schwope et al., NIDA Res Monograph Series, 1975, (4), p. 13-8.
Yolles et al., *J Pharmaceutical Sciences* Feb. 1975, 64(2) p. 348-9.
Thies, NIDA Res Monograph Series, 1975. (4), p. 19-20.
Chiang et al., *Clin. Pharmacol. Ther.* Nov. 1984. 36(5), p. 704-8.
Pitt et al., NIDA res. Monograph Series, 1981, 28, p. 232-53.
Chiang et al., *Drug & Alcohol Dependence*, Sep. 1985, 16(1) p. 1-8.
Yoburn et al., *J. Pharmacol. & Experimental Therapeutics*, Apr. 1986, 237(1) p. 126-130.
Cha and Pitt, *J. Controlled Release*, 1989, 8(3), p. 259-265.
Yamaguchi and Anderson, *J. Controlled Release*. 1992,19(1-3), p. 299-314.
Kuhlman et al., *Addiction*, 1998, 93:549-59.
Schottenfeld et al., *Arch. Gen. Psychiatry* 1997, 54:713-20.

* cited by examiner

*Primary Examiner*—Michael G. Hartley
*Assistant Examiner*—James Rogers
(74) *Attorney, Agent, or Firm*—Fish & Richardson P.C.

(57) ABSTRACT

An injectable slow-release methadone, partial opioid agonist or opioid antagonist formulation is provided comprising methadone, a partial opioid agonist or opioid antagonist in a poly(D,L-lactide) excipient with a small amount of residual ethyl acetate. Upon intramuscular or subcutaneous injection of the composition, methadone, a partial opioid agonist or opioid antagonist is released in a controlled manner over an extended period of time. The composition finds use in the treatment of heroin addicts and alcoholics to reduce consumption of the abused substances. Of particular interest are the drugs buprenorphine, methadone and naltrexone.

12 Claims, 1 Drawing Sheet

INJECTABLE METHADONE, METHADONE AND NALTREXONE, OR BUPRENORPHINE AND NALTREXONE MICROPARTICLE COMPOSITIONS AND THEIR USE IN REDUCING CONSUMPTION OF ABUSED SUBSTANCES

CROSS REFERENCE TO RELATED APPLICATIONS

This application claims the benefit of provisional application ser. No. 60/151,112, filed Aug. 27, 1999, which disclosure is incorporated herein by reference.

INTRODUCTION

BACKGROUND

The disease of substance abuse remains a scourge on society. As it becomes more evident that there is a substantial genetic contribution to becoming addicted, helping addicted individuals to terminate their dependency or at least achieve a level of becoming a functional member of society, rather than treating substance abuse as a moral issue, has become increasingly accepted policy. Various programs have been put in place in the public and private sectors. In the private sectors, there are such organizations as Alcoholics Anonymous and Narcotics Anonymous, which play an important role in psycho-social support. In addition there are many private clinics which serve to provide both psycho-social support and medicinal support, using the somewhat limited repertoire of drugs which are available. In the public arena, there are the extensive programs to bring to the attention of young people and parents the hazards of substance abuse and discourage the young people from embarking on drug use. Also, there are the methadone programs, which are primarily public supported.

The number of substance abusing subjects in the United States is quite staggering. There are estimated to be about 15 million people who abuse alcohol, about 1.3 million who abuse cocaine in its many manifestations, about 0.8 million who abuse amphetamines and about 0.5-0.8 million who abuse heroin, in addition to the use of other drugs, such as the psychedelic drugs. Efforts to reduce the numbers of scheduled substances and alcohol users have been continuous and relatively unavailing. Those subjects who have entered programs have had a dismal record of relapse, so that only a small proportion of the people who do enter programs and are retained in the programs remain clean long after the completion of the program.

One significant factor in lack of retention and relapse is compliance. A repetitive act, such as taking a pill daily, is not a simple matter, even where the subject has no qualms about taking the pill. With the substance abuser, who may have physiological and emotional needs for the abused substance, the sustaining of the therapeutic routine is substantially more difficult. Therapeutic techniques, which require perseverance on the part of the subject, decrease the likelihood of success of the treatment. It is therefore of great importance to be able to reduce the level of involvement of the subject where medicinal treatments are involved, particularly treatments which may involve frequent scheduling, monitoring of compliance, and sustaining a particular regimen.

In order to reduce the vicissitudes of compliance, there have been efforts to provide sustained-release methodologies. These have involved pumps, patches, depots and the like. Where the release implement is accessible to the subject, there is always the temptation to remove the implement during a craving episode. This opportunity, which may be an indication of will power, nevertheless, puts the subject at risk who succumbs to the temptation. By providing for a slow-release medicament which is introduced into the body, the temptation is avoided and the drug is released in accordance with a predetermined schedule over an arranged period of time. One can have implantable rods which are introduced surgically or microparticles which are injectable. Rods or microparticles can be devised to release the drug over an extended period of time in a controlled manner.

Microcapsules and microspheres are usually powders consisting of spherical particles 2 mm or less in diameter, usually 500 μm or less in diameter. If the particles are less than 1 μm, they are often referred to as nanocapsules or nanospheres. For the most part, the difference between microcapsules and nanocapsules or the difference between microspheres and nanospheres is their size.

A microcapsule or nanocapsule has its encapsulated material (hereinafter referred to as agent) centrally located within a unique membrane, usually a polymeric membrane. This membrane may be termed a wall-forming membrane, and is usually a polymeric material. Because of their internal structure, permeable microcapsules designed for controlled-release applications release their agent at a constant rate (zero-order rate of release). Also, impermeable microcapsules can be used for rupture-release applications. A microsphere has its agent dispersed throughout the particle; that is, the internal structure is a matrix of the agent and excipient, usually a polymeric excipient. Usually, controlled-release microspheres release their agent at a declining rate (first-order). But microspheres can be designed to release agents at a near zero-order rate. Microspheres tend to be more difficult to rupture as compared to microcapsules because their internal structure is stronger. Hereinafter, the term microparticles will include nanospheres, microspheres, microcapsules, nanocapsules, microbubbles (hollow particles), porous microbubbles, nanoparticles, microsponges (porous microspheres) and particles in general.

Various slow-release microparticles have been developed for a variety of drugs, but very few have been commercialized. There are many constraints on a satisfactory slow-release injectable formulation: the release of the drug must be over an extended period of time; during the time of treatment, the level of drug maintained in the subject must be an effective level, without reaching any hazardous level; the drug must be released slowly without a catastrophic dumping of the drug; the polymeric excipient used for the microparticles must be biodegradable and biocompatible; any residual chemicals must be below the maximum acceptable level; the microparticles must be small and capable of being administered by a syringe with a needle size which is acceptable to patients; the results must be reproducible, which requires that the process can be accurately controlled and is not unduly sensitive to minor changes in conditions; the injectable formulation must be sterile; and must have other characteristics which may be general or specific to the particular medicament. The properties of the microparticles are sensitive to many properties of the drug and excipient, as well as the selection of the process and the conditions under which the microparticles are prepared and subsequently processed.

Relevant Literature

Buprenorphine (N-cyclopropylmethyl-7-[1-(s)-hydroxy-1,2,2-trimethylpropyl]-6,14-endoethano-6,7,8,14-tetrahydronoroipavine) is reported as effective in the treatment of opiate addiction using sublingual administration (U.S. Pat. No. 4,935,428). Nasal administration of buprenorphine is reported in U.S. Pat. No. 4,464,378. Long-acting drug antagonists are reported in U.S. Pat. Nos. 5,716,631 and 5,858,388. The use of buprenorphine for the treatment of drug dependence has been reported in numerous publications. Kuhlman et al., *Addiction* 1998 93:549-59; Schottenfeld et al., *Arch Gen. Psychiatry* 1997, 54:713-20; Strain et al., J. Clin. Psychopharmacol 1996, 16:58-67; are illustrative of a few of the reports. The combination of buprenorphine and naloxone is reported in O'Connor et al., *Ann. Intern Med.* 1997, 127: 526-30.

Krantzler, et al., *Alcoholism:Clin and Exp Res* 1998, 22:1074-1079 report the treatment of alcoholics with a slow-release naltrexone particle injectable formulation. A number of studies were carried out by Reuning's laboratory concerning naltrexone and its use in a slow-release form: Reuning, et al., NIDA Re: Monograph Series, Jan. 1976, (4) p43-5; Reuning et al., *J. Pharmacokinet Biopharm*, August 1983, 11 (4), p369-87; Reuning, et al., *Drug Metab Dispos* November-December 1989, 17(6) p583-9; MacGregor et al., *J. Pharm Pharmacol*, January 1983, 35(1) p38-42; Reuning et al., NIDA Res Monograph Series 1980, 28, p172-84. See also, Schwope et al., NIDA Res Monograph Series, 1975, (4), p13-8; Yolles et al., *J Pharm Sci* February 1975, 64(2) p348-9; Thies, NIDA Res Monograph Series, 1975 (4), p19-20; Schwope et al., NIDA Res Monograph Series, January 1976, 4, p13-18; Chiang et al., *Clin Pharmacol Ther* November 1984 36(5) p704-8; Pitt et al., NIDA Res Monograph Series 1981, 28, p232-53; Chiang et al., Drug Alcohol Depend (SWITZERLAND), September 1985, 16 (1) pl-8; Yoburn et al., *J. Pharmacol Exp Ther*, April 1986, 237 (1) p126-130; Cha and Pitt, *J. Control Release*, 1989, 8(3), p259-265; Yamaguchi and Anderson, *J Control Release*, 1992, 19(1-3), p299-314.

The use of naltrexone in the treatment of alcoholism is described in O'Malley et al., *Psychiatric Annals*, November 1995, 11, p681-688, as well as numerous other publications.

Patents of interest include U.S. Pat. Nos. 4,568,559; 4,623,588; 4,897,267; and 5,486,362. U.S. Pat. No. 5,407,609 describes a process applicable to the process employed in the subject invention.

The use of polylactide in the preparation of drug-containing microparticles is described in Benita et al., *J Pharm Sci*, December 1984, 73(12) p1271-4; Speniehauer et al., ibid, August 1986, 75(8), p 750-5; and Nihant et al., October 1994, 11(10), p1479-84.

SUMMARY OF THE INVENTION

Injectable, slow-release partial opiod agonist and opioid antagonist formulations are provided comprising a therapeutically effective amount of partial opioid agonist or opioid antagonist (hereinafter referred to as drug or agent) released over an extended period of time and an excipient, for example, poly (D,L-lactide) polymer. The microparticles are under 125 μm in diameter and can be readily injected intramuscularly and provide at least about 0.5 ng/ml of drug over the extended period. Different release profiles are obtained depending upon the molecular weight of the polymer, the drug and the weight percentage of the drug. The microparticles are prepared by solvent extraction of a dispersed or dissolved drug polymer solution. Mixtures of microparticles of an agonist drug and an antagonist can be used to diminish any illicit use of the partial opiod agonist microparticles.

DESCRIPTION OF THE SPECIFIC EMBODIMENTS

Figure 1:
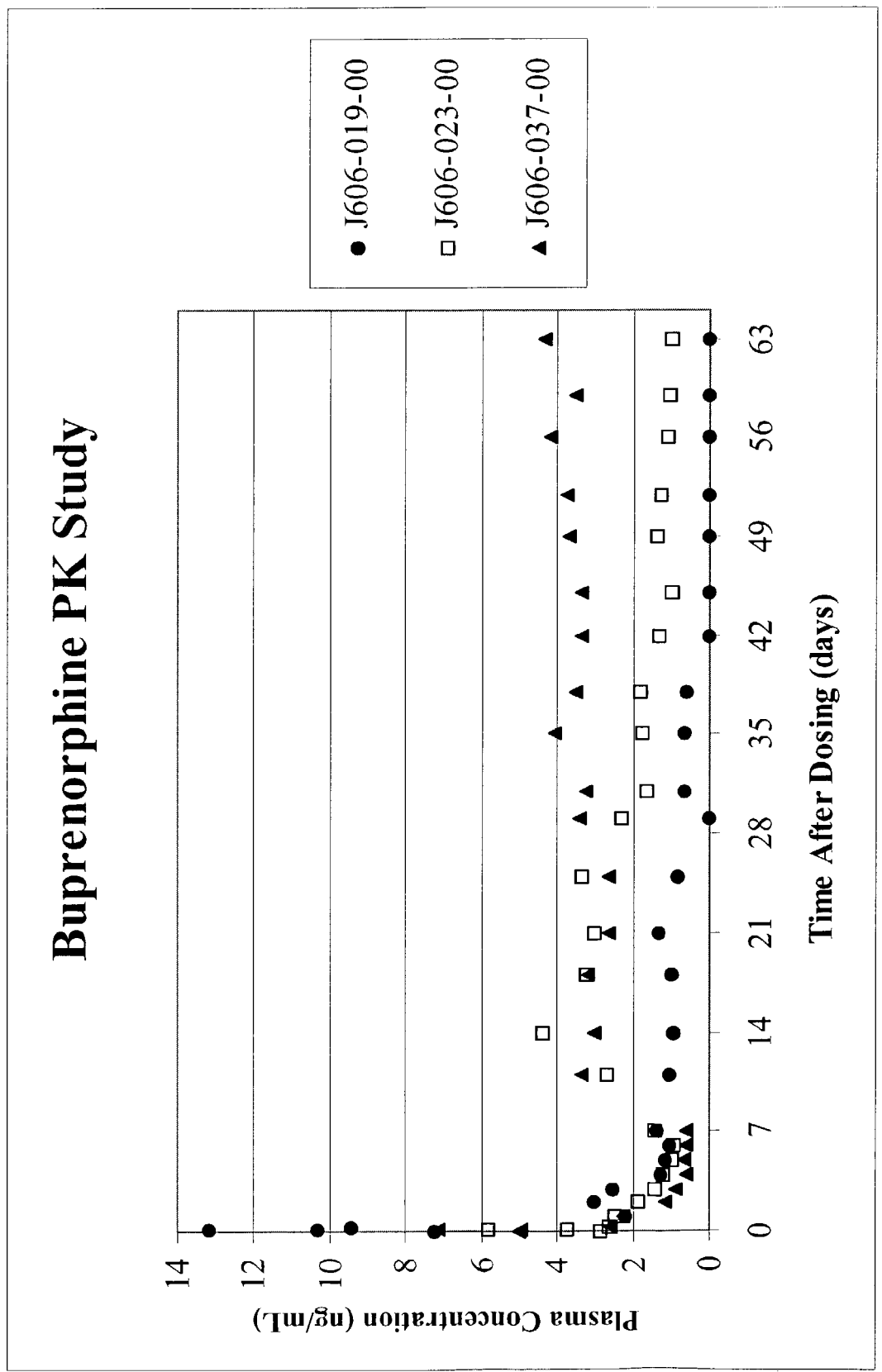
FIG. 1 compares the pharmacokinetic profiles for three different buprenorphine microparticle formulations after a single administration (25 mg/kg) in dogs.

Injectable slow-release, methadone, partial opioid agonist and/or antagonist formulations are provided for use in the treatment of alcoholics and heroin addicts and such other indications for which methadone, partial opiod agonists or antagonists have been found to be efficacious. The injectable slow-release methadone, partial opioid agonists or antagonists are characterized by having an effective plasma level in the range of about 0.5-1 ng/ml, usually 0.75-5 ng/ml, usually not more than about 3ng/ml. The partial opioid agonists include buprenorphine, and the like, while the antagonists include naltrexone.

Small sterilized microparticles are provided which can pass through a syringe needle and can be administered intramuscularly and remain at the site of injection for an extended period of time while continuously releasing a therapeutically effective amount of the drug for at least about 28 days. The release profile is found to be sensitive to the nature and amount of drug in the microparticles, the use of the free base as compared to the salt, and the inherent viscosity of the poly(D,L-lactide) excipient. The release profile appears to be less sensitive to the process conditions under which microparticles were prepared, the size distribution of the microparticles (as long as the composition substantially comprises microparticles in the range of 20 to 125 μm) and the amount of solvent retained (so long as the amount of residual organic solvent is below 3 weight %).

The microparticles, as observed by scanning electron microscope (SEM), have the drug dispersed throughout the polymeric excipient. The microparticles have less than 3 weight % of ethyl acetate, the solvent used in the preparation of the microparticles. The weight percent of drug is from 10 to 70 weight %, usually 15 to 65 weight % and varies in range depending upon the inherent viscosity of the excipient. The inherent viscosity of the polymeric excipient is in the range of about 0.3 to 1.2 dL/g, as measured in chloroform at 30° C. and a concentration of 0.5 g/dL. Where the polymeric excipient has an inherent viscosity in the range of about 0.3-0.4 dL/g, the amount of drug will be in the range of about 10 to 50 weight %, usually 15 to 50 weight %, while when the inherent viscosity is in the range of about 1.0-1.2 dL/g, usually 1.0-1.1 dL/g, the amount of drug will be in the range of about 30 to 70 weight %, usually 35 to 65 weight %. For the most part, polymers having a viscosity in the range of 0.45 to 0.95 dL/g will not be employed, generally only low-molecular weight and higher-molecular weight polymers are used.

Mixtures of the polymers and microparticles made from such polymers or mixtures of such polymers may be used so as to deliver an effective amount of drug over the desired duration of treatment. Thus, the weight % of two different polymers may range from 1:99 to 99:1, more usually 10:90 to 90:10, where the lower-molecular-weight polymer will be in lesser amount than the higher-molecular-weight polymer. Similarly, low-drug-loaded, low-molecular-weight excipient microparticles (0.3-0.4 dL/g) may be mixed with higher drug loaded, higher molecular weight (1.0-1.2 dL/g) excipient microparticles in weight ratios of 5:95 to 95:5, where the lower-molecular-weight excipient microparticles will usually be present in from about 10 to 65 weight %.

Greater than about 90 weight % of the microparticles will have a diameter in the range of about 20 to 100 μm and less than 5 weight % will have a diameter less than about 10 μm.

To reduce agglomeration, the microparticles may be coated with an antiagglomerating agent, such as mannitol, which will be employed in less than about 50 weight %, usually less than about 20 weight %, of the microparticles.

The microparticles are formulated in an appropriate vehicle to provide, depending upon the drug, from about 10 mg to 1 g, usually 50 to 750 mg of drug, for a single dose. For buprenorphine, the amount will generally be in the range of about 20 mg to 1 g, more usually from about 20 to 750 mg, while for methadone the amount will be from about 100 to 350 mg, more usually from about 150 to 250 mg, and for naltrexone will be in the range of about 150 to 300 mg. The vehicle may be sterile water, phosphate buffered saline, or other conventional vehicle for administering the microparticles. Additives may be present to improve suspendibility of the microparticles, slow the microparticles settling, and diminish discomfort from the injection. Conveniently, mannitol may be present in about 2 to 10 weight % of the vehicle, particularly 4 to 7 weight % of the vehicle. Other physiologically acceptable additives may include nonionic detergents, e.g. Tween, if present, will be present in from about 0.05 to 0.2 weight % of vehicle, viscosity enhancing agents, e.g. carboxymethylcellulose, in the range of about 0.1 to 1 weight % of vehicle, and other conventional additives, as appropriate. The amount of vehicle will generally be in the range of about 1 to 5 mL, usually 1 to 3.5 mL. The microparticles are dispersed in the vehicle immediately before use. Generally, the sterile microparticles will be stored in a sterile vial with a septum, where the microparticles may be mixed with the vehicle and then withdrawn into a syringe.

The microparticles are prepared by the process substantially as described in U.S. Pat. No. 5,407,609. The process is an emulsion-based process which involves the preparation of an emulsion comprising an aqueous continuous phase (water and a surfactant and/or thickening agent) and a hydrophobic phase (polymer solvent, polymer and drug). After formation of the emulsion, the polymer solvent is extracted into an aqueous extraction phase. After a sufficient amount of polymer solvent is extracted to harden the microparticles, the microparticles are collected on sieves and washed to remove any surfactant remaining on the surface of the microparticles. The microparticles are then dried with a nitrogen stream for an extended period, e.g. about 12 hours, then dried in a vacuum oven at room temperature until at least substantially dry, conveniently for about 3 days.

A relatively simple apparatus may be employed for the preparation of microparticles. Using storage containers for the different streams, tubing, three-way valves and a homogenizer, the system is readily assembled. In addition, various monitoring devices may be included, such as flow meters, temperature monitors, particle size monitors, etc. The organic solution is introduced into a first tube connected to a three way valve, which connects to the aqueous continuous phase and to the homogenizer. By controlling the rate of flow of the two streams into the line connecting the homogenizer, the ratio of the two streams can be controlled, as well as the residence time in the homogenizer. The effluent from the homogenizer exits through a line which connects to a three-way valve through which the water stream is introduced. Again, the rate of flow ratio controls the amount of water to the homogenizer effluent stream. The residence time of the water extraction step is controlled by the length of tubing and the rate of flow of the combined streams. The microparticles are then segregated by size by passing through two or more sieves which eliminates microparticles outside the desired range.

For the preparation of the subject microparticles, the dispersed phase contains about 1-10 weight % of the drug and about 20-weight % polymer dispersed or dissolved (hereinafter both are included when referring to the polymer in a solvent as dispersed) in ethyl acetate. The continuous phase is an aqueous solution of about 1-10 weight % of poly(vinyl alcohol) and contains ethyl acetate at 1 to 7.5 weight %. The extraction phase is water. Generally, the amount of drug employed will be from about 10 to 50 weight % in excess of the final drug in the micromicroparticles. Temperatures may be ambient, generally being from about 15 to 30° C.

After the microparticles have been collected and dried they may be stored at ambient temperatures, particularly in the range of about 0-20° C. in an oxygen and water free environment, or divided into aliquots into appropriate containers and sterilized. Various methods of sterilization may be employed, gamma irradiation being convenient.

The primary application for the subject formulations is as an intramuscular injectable, although subcutaneous injections may also be used. The subject will normally be a substance abuser, such as alcohol or heroin, but the subject compositions may be used for other indications, such as obesity. The appropriate amount of the subject formulation is directly injected into a convenient site, e.g. gluteus. Thereafter, the subject may be monitored for drug plasma concentration to ensure that the amount is in the therapeutic range. When the drug plasma concentration falls below the therapeutic range, a subsequent injection may be made and this process repeated during the treatment period.

For heroin addicts, the subject will normally be detoxified by any one of a number of different ways, using buprenorphine, clonidine, naltrexone, etc. and checking with naloxone. A response to naloxone indicates that the subject has not been completely detoxified. Depending on the drug to be administered, usually a daily regimen of the drug dose will be made for at least about 3 days and not more than about 2 weeks, to ensure that the subject does not have an adverse reaction to the slow-release detoxification drug. Once it has been established that there is no adverse reaction, the depot form of the detoxification drug may then be administered.

By having microparticles which have long-term releasing capability, that is, greater than 14 days, usually greater than about 28 days, particularly greater than about 56 days, one can layer the administration, so that by giving injections in a periodic manner, one obtains an additive effect. In this manner, smaller doses may be administered after the first dose, since one continues to obtain release from the prior injected microparticles to which is added the release from the lately administered microparticles, or one can enjoy enhanced levels of the partial opioid agonist or opioid antagonist without increasing the amount of the microparticles which are administered. By providing for microparticles that can continue to release at levels in excess of 0.5 ng/ml, usually greater than about 1 ng/ml in blood, and depending on the prescribed plasma levels, usually not exceeding about 5 ng/ml, more usually not exceeding about 3 g/ml, for greater than about 28 days after injection, preferably at least about 36 days, more preferably at least about 42 days, there can be a continuous plasma level, where the plasma level of the drug may be maintained in the therapeutic range. In this way, protection is greatly enhanced, as the subject is continuously exposed to a protective level of the drug and one can provide levels of the drug, which will inhibit response to a 50 mg challenge dose of heroin.

The following examples are offered by way of illustration and not by way of limitation.

EXAMPLES

Example 1

General Method of Preparation of Naltrexone Microparticles

The following example is exemplary of the method of preparation generally, where the individual conditions are indicated in the following table. The chemical components are prepared as follows. Poly(D,L-lactide) is dissolved in ethyl acetate with stirring. The drug is added to the polymer solution and dissolved with stirring. Poly(vinyl alcohol) ("PVA") is dissolved in sterile water by slowly adding the PVA to the stirred water while heating the sterile water to a temperature of 90° C. After complete dissolution of the PVA, the solution is allowed to cool and filtered through a 0.2 μm filter, which is followed by adding ethyl acetate to the PVA solution at 3 wt. %.

The system employed is substantially as described above, where for a batch of 15 g, using polymer having a viscosity of 1.07 dL/g and a theoretical drug concentration of 50% (relative to the combined weight of polymer and drug), the tubing employed is 0.5 inches i.d., and the length of the tubing for the final water extraction is 200 ft.

The equipment is set up as follows. The organic solution at a temperature of about 20° C. is pumped into the influent tubing at about 6 g/min. The PVA solution at about 20° C. is pumped into the influent tubing downstream from the organic solution at a rate of about 65 g/min. An emulsion is formed by continuously feeding this solution into a homogenizer. The effluent stream is diluted with sterile water at about 20° C., which is pumped into the effluent stream at a rate of about 2000 g/min through tubing having sufficient length so as to provide an extraction time of about 6 minutes. The resulting microparticles are collected as particles which pass through a 125-μm sieve and are collected by a 20-μm sieve. The microparticles are continuously stirred and rinsed with sterile water to prevent premature drying. After ensuring that there are no more microparticles exiting the homogenizer, the homogenizer is stopped and the microparticles are rinsed with sterile water until there is no further PVA present.

After rinsing with sterile water the microparticles collected on the 20-mm sieve are dried under vacuum at room temperature for about 3 days. Dried product is obtained after a final sieving of the microparticles through a 125-μm sieve.

To reduce any agglomeration, the microparticles may be mixed with or thinly coated with mannitol. The microparticles may then be dispersed in an appropriate vehicle of sterile water comprising 0.5% carboxymethyl cellulose, 0.1% Tween 80 and 5.0% mannitol. The volume will be in the range of 1-3.5 mL to obtain satisfactory dispersion and release through an 18-gauge needle.

The following table indicates specific parameters for the preparation of the microparticles and the properties and performance of the microparticles in vitro and in vivo. In the in vivo study, dogs were injected intramuscularly with an 18-gauge needle with about 2 mL of solution containing the microparticles at the weight indicated in the table. The plasma was monitored for naltrexone at the times indicated. For the in vitro study, microparticles were maintained in 0.01M phosphate buffer, pH 7.4 at 37° C. and the residual naltrexone in the microparticles determined at the times indicated.

TABLE 1

| Lot no. | Dog ID | Target naltrexone | Actual naltrexone | Encapsulation efficiency % | Temperature °C. | Polymer inherent viscosity dl/g,[e] | Mean particle size, μm |
|---|---|---|---|---|---|---|---|
| 74 | | 25 | 17.9 | 69 | | 0.36 | 45.46 |
| 98[a] | 2068-AM 2078-AM | 25 | 17 | 68 | | 0.36 | 58.54 |
| 82 | | 35 | 20.5 | 59 | | 0.36 | 32.44 |
| 84 | | 50 | 31.9 | 64 | | 0.36 | 56.71 |
| 94 | | 25 | 16 | 64 | | 0.67 | 59.75 |
| 100 | | 35 | 22.7 | 65 | | 0.67 | 41.56 |
| 102 | | 50 | 45.2 | 91 | | 0.67 | 47.56 |
| 114 | 2071-BM 2074-BM 2069-CM | 60 | 52.7 | 88 | | 0.67 | 56.36 |
| 130 | | 70 | 59.4 | 85 | | 0.67 | 56.34 |
| 132[b] | | 70 | 45 | 64 | | 0.67 | 59.69 |
| 90 | | 25 | 16.6 | 66 | | 1.07 | 45.3 |
| 88 | | 35 | 29.9 | 85 | | 1.07 | 54.47 |
| 92 | 2062-HM 2067-HM 2073-HM | 50 | 38.3 | 77 | | 1.07 | 57.76 |
| 140 | | 50 | 42.7 | 85 | | 1.07 | 55.52 |
| 142 | 2063-JM 2066-JM 2070-KM | 50 | 42.5 | 85 | | 1.07 | 44.36 |
| 116[c] | 2064-DM 2076-DM 2077-EM | 60 | 52.9 | 88 | 11 | 1.07 | 51.08 |
| 118[d] | 2065-FM 2072-FM 2075-GM | 60 | 49 | 82 | 22 | 1.07 | 39.78 |
| 128 | | 70 | 62.1 | 89 | | 1.07 | 55.14 |

[a] remake of 74
[b] batch prepared with dispersed drug
[c] continuous phase was chilled to 11° C. and did not contain ethyl acetate
[d] continuous phase was at room temperature (22° C.) and water saturated with 3% ethyl acetate
[e] inherent viscosity measured in $CHCl_3$ at 30° C. at a concentration of 0.5 dL/g
[f] Injection vehicle contained 2 wt. % sodium carboxymethyl cellulose and 1 wt. % Tween

TABLE 2

| Lot no. | Naltrexone dose, mg | Microsphere dose | Vehicle ml[f] | Naltrexone in plasma ng/ml 1 hr | 2 hrs | 4 hrs | 8 hrs | 24 hrs | 48 hrs |
|---|---|---|---|---|---|---|---|---|---|
| 74 | | | | | | | | | |
| 98 | 118.5 | 697.1 | 1.7 | 19.53 | 10.6 | | 2.23 | 2.37 | 2.57 |
|  | 127.5 | 750 | 1.6 | 21.46 | 12.08 | | 2.22 | 1.6 | 2 |
| 82 | | | | | | 6.84 | | | |
| 84 | | | | | | | | | |
| 94 | | | | | | | | | |
| 100 | | | | | | | | | |
| 102 | | | | | | | | | |
| 114 | 136.5 | 259 | 1.9 | 30.93 | 22.57 | 14.25 | 6.84 | 7.38 | 9 |
|  | 132 | 250.5 | 1.9 | 24.7 | 15.45 | 11.47 | 6.13 | 5.57 | 6.3 |
|  | 240.8 | 456.8 | 1.8 | 29.98 | 22.77 | 13.2 | 8.97 | 6.51 | 8.37 |
| 130 | | | | | 23.08 | | | | |
| 132 | | | | | | | | | |
| 90 | | | | | | | | | |
| 88 | | | | | | | | | |
| 92 | 165 | 430.8 | 1.8 | 6.8 | 2.79 | 1.82 | 0.73 | 0.82 | 0.81 |
|  | 147 | 383.8 | 1.8 | 6.33 | 4.14 | 2.34 | 0.64 | BQL | 0.86 |
|  | 202.5 | 528.7 | 1.7 | 9.66 | 5.28 | 2.41 | 0.89 | 1.13 | 0.61 |
| 140 | | | | | | | | | |
| 142 | 135 | 317.6 | 1.8 | 6.22 | 4.14 | 2.27 | 0.67 | 1.24 | 1.23 |
|  | 165 | 388.2 | 1.8 | 5.19 | 3.5 | 2.33 | 0.68 | 0.72 | 1.04 |
|  | 240.89 | 566.5 | 1.7 | 17.28 | 9.02 | 3.21 | 1.35 | 1.02 | 0.84 |
| 116 | 160.5 | 303.4 | 1.8 | 21.42 | 12.65 | 5.54 | 2.25 | 2.48 | 3.33 |
|  | 168 | 317.6 | 1.8 | 18.18 | 9.6 | 4.4 | 1.57 | 1.78 | 2.46 |
|  | 220.5 | 416.8 | 1.8 | 34 | 17.45 | 9.92 | 3.39 | 5.78 | 6.88 |
| 118 | 165 | 336.7 | 1.8 | 15.56 | 9.04 | 4.53 | 1.25 | 1.81 | 1.8 |
|  | 133.5 | 272.4 | 1.9 | 7.6 | 4.04 | 1.77 | 0.79 | 0.71 | 0.9 |
|  | 225 | 459.2 | 1.8 | 13.02 | 7.16 | 3.2 | 1.02 | 1.41 | 1.28 |
| 128 | | | | | | | | | |

[a] remake of 74
[b] batch prepared with dispersed drug
[c] continuous phase was chilled to 11° C. and did not contain ethyl acetate
[d] continuous phase was at room temperature (22° C.) and water saturated with 3% ethyl acetate.
[e] inherent viscosity measured in $CHCl_3$ at 30° C. at a concentration of 0.5 dL/g
[f] Injection vehicle contained 2 wt. % sodium carboxymethyl cellulose and 1 wt. % Tween

TABLE 3

| Lot no. | Naltrexone in plasma ng/ml 3 days | 7 days | 11 days | 14 days | 18 days | 21 days | 29 days | 35 days |
|---|---|---|---|---|---|---|---|---|
| 74 | | | | | | | | |
| 98[a] | 3.06 | 3.33 | 1.86 | BQL | 1.13 | 0.76 | 0.95 | 1.01 |
|  | 2.9 | 3.35 | 3.51 | 2.73 | 2 | 1.36 | 1.83 | 1.79 |
| 82 | | | | | | | | |
| 84 | | | | | | | | |
| 94 | | | | | | | | |
| 100 | | | | | | | | |
| 102 | | | | | | | | |
| 114 | 20.56 | 35.67 | BQL | BQL | 1.43 | BQL | BQL | |
|  | 11.64 | 22.62 | 0.88 | BQL | BQL | BQL | BQL | |
|  | 10.5 | 33.35 | 2.04 | BQL | BQL | BQL | BQL | |
| 130 | | | | | | | | |
| 132 | | | | | | | | |
| 90 | | | | | | | | |
| 88 | | | | | | | | |
| 92 | 1.17 | 24.95 | 5.14 | 3.99 | 3.27 | 3.63 | 1.38 | 0.7 |
|  | 0.62 | 18.04 | 11.13 | 7.22 | 4.87 | 3.42 | 1.8 | 1.55 |
|  | 1.29 | 55.3 | 17.71 | 7.74 | 4.43 | 4.2 | 1.26 | NA |
| 140 | | | | | | | | |
| 142 | 1.55 | 35.49 | 7.7 | 2.79 | 1.74 | 1.31 | 0.99 | 0.86 |
|  | 1.03 | 23.3 | 5.82 | 2.38 | 2.1 | 2.15 | 1.46 | 0.87 |
|  | 1.14 | 38.34 | 11.98 | 2.73 | 7.18 | 5.74 | 1.8 | NA |
| 116d | 11.39 | 26.97 | 5.68 | 1.59 | 0.81 | BQL | BQL | |
|  | 5.58 | 18.27 | 5.34 | 1.44 | 0.64 | BQL | BQL | |
|  | 13.7 | 53.02 | 4.84 | 1.54 | 0.57 | BQL | BQL | |

TABLE 3-continued

| Lot no. | Naltrexone in plasma ng/ml 3 days | 7 days | 11 days | 14 days | 18 days | 21 days | 29 days | 35 days |
|---|---|---|---|---|---|---|---|---|
| 118e | 2.44 | 51.3 | 7.17 | 4.65 | 1.22 | BQL | BQL | |
| | 1.02 | 28.4 | 1.98 | 0.71 | BQL | BQL | BQL | |
| 128 | 2.21 | 35.01 | 5.63 | 2.07 | 1.44 | 0.54 | BQL | |

BQL = Below quantitation level
[a] remake of 74
[b] batch prepared with dispersed drug
[c] continuous phase was chilled to 11° C. and did not contain ethyl acetate
[d] continuous phase was at room temperature (22° C.) and water saturated with 3% ethyl acetate
[e] inherent viscosity measured in $CHCl_3$ at 30° C. at a concentration of 0.5 dl/g
[f] Injection vehicle contained 2 wt. % sodium carboxymethyl cellulose and 1 wt. % Tween Lot 98 was above the quantitation level of 0.5 ng/ml out to 140 days, while lots 82 and 142 were above the quantitation level up to 49 days.

Example 2

Preparation of Buprenorphine (Free-base) Microparticles

A typical 10 g batch size was prepared as follows:

A 7% polymer solution was prepared by dissolving 5 g polymer in 66.2 g ethyl acetate. To this solution, 5 g of buprenorphine was added. This mixture (the dispersed phase, DP) was stirred until the drug dissolved.

A solution of 2 wt % poly(vinyl alcohol) was prepared in water. Sufficient ethyl acetate was added to this solution in order that the final concentration of ethyl acetate was 2.5 wt %. This solution (the continuous phase, CP) is called the CP phase.

The DP was pumped into a mixer at 27.2 g/min. Using separate tubing, the CP was pumped into the mixer as well at a flow rate of 124 g/min. The two solutions were kept separate until immediately before mixing took place inside the continuous-flow mixer head. Mixing was performed at a stir speed of 870 rpm. The emulsion coming out of the mixer was extracted using water that was pumped at a rate of 2050 g/min to form a microparticle suspension. The suspension was collected, by hand, across 125-μm and 25-μm sieves. The portion of microparticles collected on the 25-μm screen was added to a tank of fresh water and stirred for 3 hours under ambient conditions. The microparticles were again collected by sieving and the portion obtained on the 25-μm screen was removed and dried by lyophilization. The final dried powder passed through a 125-μm sieve and was characterized with respect to drug content and particle size distribution (See Table 4).

Example 3

Preparation of Buprenorphine (Free-base) Microparticles

A typical 20 g batch size was prepared as follows:

A 4.1% polymer solution was prepared by dissolving 6.3 g polymer in 146.6 g ethyl acetate. To this solution, 11.6 g of buprenorphine was added. This mixture (the dispersed phase, DP) was stirred until the drug dissolved.

A solution of 1 wt % poly(vinyl alcohol) was prepared in water. Sufficient ethyl acetate was added to this solution in order that the final concentration of ethyl acetate was 2.5 wt %. This solution (the continuous phase, CP) is called the CP phase.

The DP was pumped into a mixer at 25.9 g/min. Using separate tubing, the CP was pumped into the mixer as well at a flow rate of 127.2 g/min. The two solutions were kept separate until immediately before mixing took place inside the continuous-flow mixer head. Mixing was performed at a stir speed of 726 rpm. The emulsion coming out of the mixer was extracted using water that was pumped at a rate of 2038 g/min to form a microparticle suspension. The suspension was collected, by hand, across 125-μm and 25-μm sieves. The portion of microparticles collected on the 25-μm screen was added to a tank of fresh water and stirred for 3 hours under ambient conditions. The microparticles were again collected by sieving and the portion obtained on the 25-μm screen was removed and dried by lyophilization. The final dried powder passed through a 125-μm sieve and was characterized with respect to drug content and particle size distribution (See Table 4).

TABLE 4

Characterization of Buprenorphine Microspheres

| Lot Number | Poly(DL-lactide) IV, dL/g[a] | Drug content, wt % buprenorphine | Mean particle size, μm |
|---|---|---|---|
| J606-019-00 | 0.37 | 21.2 | 52.8 |
| J606-023-00 | 0.37 | 43.1 | 57.2 |
| J606-037-00 | 1.07 | 44.1 | 63.1 |
| J606-103-00 | 1.07 | 60.9 | 64.9 |

[a] IV = inherent viscosity (chloroform, 0.5 g/dL, 30° C.)

Pharmacokinetics of a single administration in dogs (25 mg buprenorphine/kg) was measured using microparticles that received about 2.5 Mrad gamma-irradiation.

TABLE 5

Pharmacokinetic Data in Dogs

| | Buprenorphine plasma conc, ng/mL | | |
|---|---|---|---|
| Time | J606-019-00 | J606-023-00 | J606-037-00 |
| 1 hr | 7.23 | 2.86 | 4.98 |
| 2 hr | 10.3 | 5.80 | 7.13 |

TABLE 5-continued

Pharmacokinetic Data in Dogs

| | Buprenorphine plasma conc, ng/mL | | |
|---|---|---|---|
| Time | J606-019-00 | J606-023-00 | J606-037-00 |
| 4 hr | 13.2 | 3.75 | 4.92 |
| 8 hr | 9.42 | 2.62 | 2.58 |
| 24 hr | 2.22 | 2.45 | 2.27 |
| 48 hr | 3.01 | 1.85 | 1.15 |
| 72 hr | 2.54 | 1.42 | 0.86 |
| Day 5 | 1.26 | 1.22 | 0.6 |
| Day 6 | 1.16 | 0.98 | 0.66 |
| Day 7 | 1.03 | 0.94 | 0.6 |
| Day 8 | 1.39 | 1.45 | 0.59 |
| Day 12 | 1.05 | 2.71 | 3.37 |
| Day 15 | 0.96 | 4.41 | 3.02 |
| Day 19 | 1.00 | 3.25 | 3.21 |
| Day 22 | 1.30 | 3.01 | 2.64 |
| Day 26 | 0.81 | 3.33 | 2.62 |
| Day 30 | BQL[a] | 2.33 | 3.40 |
| Day 32 | 0.66 | 1.63 | 3.25 |
| Day 36 | 0.68 | 1.75 | 4.04 |
| Day 39 | 0.58 | 1.82 | 3.53 |
| Day 43 | BQL | 1.30 | 3.34 |
| Day 46 | BQL | 1.00 | 3.35 |
| Day 50 | BQL | 1.36 | 3.66 |
| Day 53 | BQL | 1.26 | 3.74 |
| Day 57 | BQL | 1.12 | 4.18 |
| Day 60 | BQL | 1.03 | 3.53 |
| Day 64 | BQL | 0.98 | 4.32 |

[a]BQL = below quantitation limit of 0.5 ng/mL

It is evident from the above results that a long term supply of a partial opiod agonist or opioid antagonist at a physiologically effective concentration can be provided in vivo. In this way, compliance problems associated with the requirement of taking a pill daily can be avoided. Monitoring to determine whether the subject has taken the daily pill is obviated. The subject is better able to deal with the problem of substance abuse, being aware that the subject has better control in the case of alcoholism and will not obtain the desired euphoria from heroin. Counseling can be more effectively performed, since the subject will be discouraged from taking heroin and in the case of alcoholism, will be better able to cope with fewer drinks. In this way, subjects will be able to function and fulfill their obligations to their families and society.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A slow release formulation comprising:
a mixture of a first population of microspheres and a second population of microspheres, wherein said first population comprises a buprenorphine and a residual amount of ethyl acetate that is from about 0.1 to about 3 weight %, and said second population comprises an naltrexone and a residual amount of ethyl acetate that is less than about 3 weight % ethyl acetate, and wherein said mixture provides a therapeutically effective dose of medication for the treatment of at least one of heroin and alcohol abuse for a period of at least 28 days when said slow release formulation is introduced into a mammal.

2. A microparticle composition comprising methadone in an amount in the range of 10 to 70 weight %, poly(D,L-lactide) as an excipient, and a residual amount of ethyl acetate that is from about 0.1 to about 3 weight %, capable of providing a physiologically effective plasma level over a period of at least about 28 days of said methadone to reduce the consumption of at least one of heroin and alcohol when administered intramuscularly or subcutaneously in a mammal, at least 90 weight % of said microparticle composition comprising microparticles having a diameter in the range of 20 to 125 μm.

3. The microparticle composition according to claim 2, wherein said methadone is present in an amount in the range of 15 to 50 weight%, and said poly(D,L-lactide) has an inherent viscosity in the range of about 0.3 to 0.4 dL/g.

4. The microparticle composition according to claim 2, wherein said methadone is present in an amount in the range of 30 to 65 weight %, and said poly(D,L-lactide) has an inherent viscosity in the range of about 1.0 to 1.1 dL/g.

5. The microparticle composition according to claim 2, wherein said poly(D,L-lactide) is a mixture of poly(D,L-lactide)s of differing inherent viscosities.

6. The microparticle composition according to claim 2, wherein said composition is a mixture of microparticles which differ in at least one of weight % of said methadone or poly(D,L-lactide)s of differing inherent viscosities.

7. The microparticle composition according to claim 2, wherein said microparticles are prepared by introducing a solution of said methadone and poly(D,L-lactide) in ethyl acetate into an aqueous ethyl acetate containing solution of poly(vinyl alcohol) to form an emulsion and adding said emulsion to water to extract ethyl acetate to form microparticles, and isolating the resulting microparticles.

8. A formulation for injection comprising a microparticle composition according to claim 2, carboxymethyl cellulose, Tween and mannitol.

9. A method for reducing the consumption of heroin and/or alcohol by a subject abusing at least one of heroin and alcohol, said method comprising:
administering intramuscularly or subcutaneously an effective dose of a microparticle composition according to claim 2 in an amount to inhibit the consumption of heroin and alcohol, whereby the consumption of heroin and/or alcohol is reduced.

10. A method for reducing the consumption of heroin and alcohol by a subject abusing at least one of heroin and alcohol, said method comprising:
administering an effective dose of a microparticle composition according to claim 2, which composition continues to release said methadone for a period greater than 28 days at at least an effective dose;
prior to the level of said methadone falling below an effective dose, administering a second dose of said microparticle composition, whereby the combination of said original effective dose and said second dose provide an effective dose of said methadone for a second period of at least an additional 28 days; and
repeating said administration to have said methadone being released from both a prior administration of said microparticle composition and the lately administered microparticle composition to maintain said effective dose of said methadone.

11. The method according to claim 10, wherein at least one of said period and said second period is about 60 days.

12. A slow release formulation comprising:
a mixture of a first population of microspheres and a second population of microspheres, wherein said first population comprises methadone and a residual amount of ethyl acetate that is from about 0.1 to about 3 weight %, and said second population comprises an opioid antagonist and a residual amount of ethyl acetate that is from about 0.1 to about 3 weight %, and wherein said mixture provides a therapeutically effective dose of medication for the treatment of at least one heroin and alcohol abuse for a period of at least 28 days when said slow release formulation is introduced into a mammal.

* * * * *

UNITED STATES PATENT AND TRADEMARK OFFICE
CERTIFICATE OF CORRECTION

PATENT NO. : 7,473,431 B2  
APPLICATION NO. : 10/324062  
DATED : January 6, 2009  
INVENTOR(S) : Tice et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 598 days Delete the phrase "by 598 days" and insert -- by 218 days --

Signed and Sealed this

Twenty-seventh Day of April, 2010

David J. Kappos  
*Director of the United States Patent and Trademark Office*